(12) United States Patent
Beebe et al.

(10) Patent No.: US 12,227,739 B2
(45) Date of Patent: Feb. 18, 2025

(54) DEVICE FOR FACILITATING THE ISOLATION OF TARGETS FROM A BIOLOGICAL SAMPLE

(71) Applicants: Wisconsin Alumni Research Foundation, Madison, WI (US); Salus Discovery LLC, Madison, WI (US)

(72) Inventors: David J. Beebe, Monona, WI (US); David J Guckenberger, Jr., Oconomowoc, WI (US); Hannah M Pezzi, New Berlin, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 91 days.

(21) Appl. No.: 16/784,898

(22) Filed: Feb. 7, 2020

(65) Prior Publication Data
US 2020/0231961 A1     Jul. 23, 2020

Related U.S. Application Data

(62) Division of application No. 15/370,375, filed on Dec. 6, 2016, now Pat. No. 10,590,409.

(51) Int. Cl.
*C12N 15/10* (2006.01)
*G01N 33/543* (2006.01)
*C12Q 1/6806* (2018.01)

(52) U.S. Cl.
CPC ... *C12N 15/1013* (2013.01); *G01N 33/54333* (2013.01); *C12Q 1/6806* (2013.01)

(58) Field of Classification Search
CPC ....... B03C 1/01; B03C 1/288; B03C 2201/18; B03C 1/0332; G01N 33/54326; G01N 33/54333; C12Q 1/6806; C12Q 2563/155; B01L 2200/0631; C12N 15/1013
See application file for complete search history.

(56) References Cited

U.S. PATENT DOCUMENTS

| | | | |
|---|---|---|---|
| 5,091,206 A * | 2/1992 | Wang | B01J 8/008 427/128 |
| 5,998,224 A | 12/1999 | Rohr et al. | |
| 6,033,574 A | 3/2000 | Siddiqi | |
| 6,500,343 B2 | 12/2002 | Siddiqi | |
| 2005/0244954 A1 | 11/2005 | Blackburn et al. | |
| 2005/0250141 A1 | 11/2005 | Lambert et al. | |
| 2008/0160622 A1 | 7/2008 | Su et al. | |
| 2008/0160634 A1 | 7/2008 | Su et al. | |
| 2009/0246782 A1 * | 10/2009 | Kelso | B01L 3/50851 435/6.16 |
| 2009/0325192 A1 * | 12/2009 | Kirakossian | G01N 21/6428 356/417 |
| 2010/0314572 A1 * | 12/2010 | Bose | F16F 1/361 451/28 |
| 2012/0019240 A1 * | 1/2012 | Muller | G01N 33/54326 324/244 |
| 2012/0329124 A1 | 12/2012 | Tajima | |
| 2013/0029355 A1 * | 1/2013 | Cho | G01N 27/72 977/773 |
| 2014/0100136 A1 | 4/2014 | Clarizia et al. | |
| 2014/0202960 A1 * | 7/2014 | Nishijima | B03C 1/30 210/695 |
| 2014/0248712 A1 * | 9/2014 | Rida | G01N 33/54333 436/501 |
| 2017/0073667 A1 | 3/2017 | Ohashi et al. | |
| 2017/0152509 A1 * | 6/2017 | Ohashi | C12Q 1/6806 |

FOREIGN PATENT DOCUMENTS

WO    WO-2015177933 A1 * 11/2015 ............. C12N 13/00

OTHER PUBLICATIONS

Sperotech website (Year: 2019).*

* cited by examiner

*Primary Examiner* — Narayan K Bhat
(74) *Attorney, Agent, or Firm* — Boyle Fredrickson, S.C.

(57) ABSTRACT

A method and a device are provided for facilitating the disaggregation of a plurality of solid phase substrate as the plurality of solid phase substrate are transferred from a first location to a second location. A plurality of solid phase substrate are deposited at the first location and a plurality of particles are added to the plurality of solid phase substrate. A force is generated to draw the plurality of solid phase substrate from the first location to a second location. The plurality of particles causes clumps of the plurality of solid phase substrate to break apart as the plurality of solid phase substrate are moved in response to the force.

5 Claims, 1 Drawing Sheet

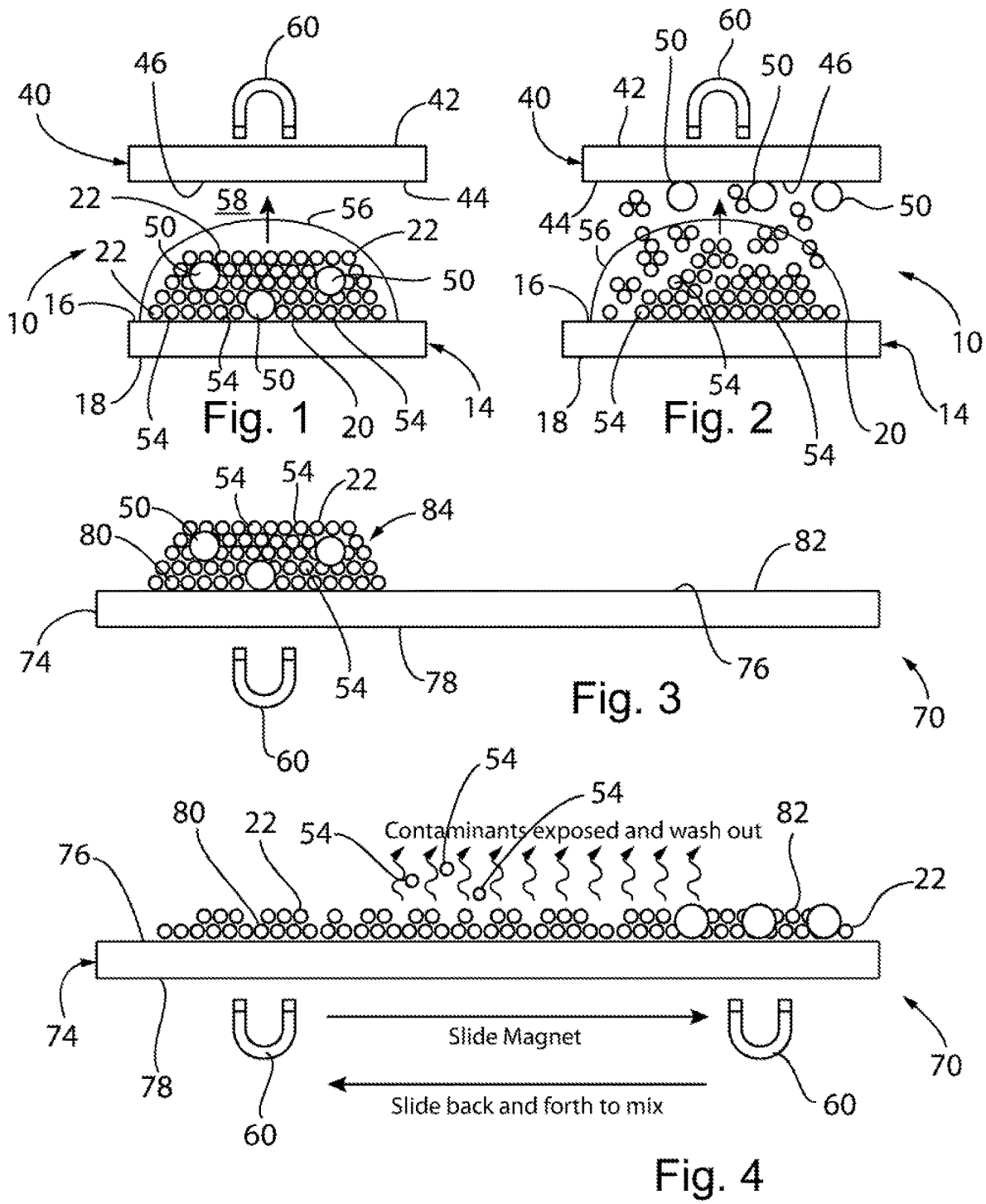

DEVICE FOR FACILITATING THE ISOLATION OF TARGETS FROM A BIOLOGICAL SAMPLE

CROSS-REFERENCE TO RELATED APPLICATION

This application is a division of U.S. application Ser. No. 15/370,375, filed Dec. 6, 2016, the entirety of which is incorporated herein.

REFERENCE TO GOVERNMENT GRANT

This invention was made with government support under CA 181648 awarded by the National Institutes of Health. The government has certain rights in the invention.

FIELD OF THE INVENTION

This invention relates generally to analyte isolation and sample preparation, and in particular, to a method and a device for the disaggregation of particles in a fluidic medium to facilitate the downstream analysis of an analyte and/or target sample.

BACKGROUND AND SUMMARY OF THE INVENTION

Methods for isolating DNA, RNA, and proteins from complex biological samples are some of the most crucial steps in molecular biology and magnetic particles are a key tool for analyte (e.g., DNA, RNA, Cells) isolation and sample preparation. The ability to use functionalized paramagnetic particles (PMPs) to isolate analytes of interest has expanded the utility of isolation methods across a range of platforms. Typically, the magnetic separation process typically involves mixing the sample with paramagnetic particles in a liquid medium to bind the target substance by affinity reaction, and then separating the bound particle/target complex from the sample medium by applying a magnetic field.

Siddiqi, U.S. Pat. No. 6,500,343 discloses an apparatus and method for carrying out the affinity separation of a target substance from a liquid test medium by mixing magnetic particles having surface immobilized ligand or receptor within the test medium to promote an affinity binding reaction between the ligand and the target substance. The test medium with the magnetic particles in a suitable container is removably mounted in an apparatus that creates a magnetic field gradient in the test medium. This magnetic gradient is used to induce the magnetic particles to move, thereby effecting mixing. The mixing is achieved either by movement of a magnet relative to a stationary container or movement of the container relative to a stationary magnet. In either case, the magnetic particles experience a continuous angular position change with the magnet. Concurrently with the relative angular movement between the magnet and the magnetic particles, the magnet is also moved along the length of the container causing the magnetic field gradient to sweep the entire length of the container. After the desired time sufficient for the affinity reaction to occur, movement of the magnetic gradient is ended, whereby the magnetic particles are immobilized on the inside wall of the container nearest to the magnetic source. The remaining test medium is removed while the magnetic particles are retained on the wall of the container. The test medium or the particles may then be subjected to further processing.

It can be appreciated that some affinity separation processes, as heretofore described, may be conducted in "sticky" mediums, thereby causing the magnetic particles to clump together and stick to surfaces (e.g., the side of a tube, face of a plate). The clumps of magnetic particles inevitably capture contaminants, which inhibit downstream analysis (e.g., nanodrop DNA quantification, PCR, etc.). Further, due to the stickiness of the clump, it may be difficult to break up the aggregate of the magnetic particles. As such, in order to break up the aggregate of the magnetic particles, the external agitation of the magnetic particles through pipetting is often required. However, the external agitation of the magnetic particles is not always effective, increases chances of sample loss, and adds time to the sample preparation process.

Therefore, it is a primary object and feature of the present invention to provide a method and a device for the disaggregation of particles in a fluidic medium to facilitate the downstream analysis of an analyte.

It is a further object and feature of the present invention to provide a method and a device for the disaggregation of particles in a fluidic medium to facilitate the downstream analysis of an analyte which reduces and/or eliminates use of external agitation with a pipette.

It is a still further object and feature of the present invention to provide a method and a device for the disaggregation of particles in a fluidic medium to facilitate the downstream analysis of an analyte which is inexpensive and simple.

In accordance with the present invention, a method is provided of reducing the clumping of a plurality of solid phase substrate as the plurality of solid phase substrate are transferred from a first location to a second location. Each solid phase substrate has a dimension. The method includes the step of depositing the plurality of solid phase substrate at the first location. A plurality of particles is added to the plurality of solid phase substrate. Each of the plurality of particles may have a dimension greater than the dimensions of the plurality of solid phase substrate. A force is generated to draw the plurality of solid phase substrate from the first location to a second location. The plurality of particles cause at least a portion of the plurality of solid phase substrate to separate from each other as the plurality of solid phase substrate is drawn from the first location to the second location.

The plurality of particles may be magnetic and the force generated may be a magnetic force. Alternatively, the plurality of particles may be non-magnetic. The plurality of solid phase substrate may be magnetic beads and the plurality of particles may be generally spherical. The step of adding the plurality of particles to the plurality of solid phase substrate may occur prior to the step of depositing the plurality of solid phase substrate at the first location.

In accordance with a further aspect of the present invention, a method is provided of reducing the clumping of a plurality of solid phase substrate as the plurality of solid phase substrate are transferred from a first location to a second location. The method includes the steps of depositing the plurality of solid phase substrate at the first location and adding a plurality of particles to the plurality of solid phase substrate to form a mixture. A force is generated to draw the mixture from the first location to a second location. The force causes the plurality of particles of the mixture to travel to the second location at a velocity greater than a velocity at which the plurality of solid phase substrate of the mixture travels to the second location.

The plurality of particles may be magnetic and the force generated may be a magnetic force. Alternatively, the plurality of particles may be non-magnetic. The plurality of solid phase substrate may be magnetic beads and the plurality of particles may be generally spherical. The step of adding the plurality of particles to the plurality of solid phase substrate may occur prior to the step of depositing the plurality of solid phase substrate at the first location. Each of the plurality of particles has a dimension and each of the plurality of solid phase substrate has a dimension. The dimensions of the plurality of particles may be greater than the dimensions of the plurality of solid phase substrate.

In accordance with a still further aspect of the present invention, a device is provided for facilitating the isolation of targets from a biological sample. The device includes a plurality of solid phase substrate. The targets are bindable to the plurality of solid phase substrate and the plurality of solid phase substrate are movable in response to a magnetic force. A plurality of particles are addable to the plurality of solid phase substrate. The plurality of particles break apart clumps of the plurality of solid phase substrate as the plurality of solid phase substrate are moved in response to the magnetic force.

Each of the plurality of particles has a dimension and each of the plurality of solid phase substrate has a dimension. The dimensions of the plurality of particles may be greater than the dimensions of the plurality of solid phase substrate. Each of the plurality of particles has an outer surface and a coating about the outer surface. The coating may be magnetic. The plurality of solid phase substrate may be magnetic beads and the plurality of particles may be generally spherical.

BRIEF DESCRIPTION OF THE DRAWINGS

The drawings furnished herewith illustrate a preferred construction of the present invention in which the above aspects, advantages and features are clearly disclosed as well as others which will be readily understood from the following description of the illustrated embodiments.

In the drawings:

FIG. 1 is a schematic view of a device for effectuating the methodology of the present invention wherein desired targets bound to corresponding magnetic beads may be transferred from a first location to a second location;

FIG. 2 is a schematic view of the device of FIG. 1 showing the disaggregation of the magnetic beads as the magnetic beads are transferred from a first location to a second location;

FIG. 3 is a schematic view of an alternate device for effectuating the methodology of the present invention; and FIG. 4 is a schematic view of the device of FIG. 3 showing the disaggregation of the magnetic beads as the magnetic beads are transferred along a surface of the device.

DETAILED DESCRIPTION OF THE DRAWINGS

Referring to FIGS. 1-2, a device for transferring a target, such as an analyte or the like, from a first location, such as a first fluid or a first surface to a second location such as a second fluid or a second surface to facilitate the disaggregation of magnetic beads to which the target is bound is generally designated by the reference numeral 10. In the depicted embodiment, device 10 includes lower plate 14 having upper and lower surfaces 16 and 18, respectively. Upper surface 16 of lower plate 14 includes first region 20 for receiving a solid phase substrate, such as a plurality of magnetic beads 22 thereon, as hereinafter described. Each of the plurality of magnetic beads has a diameter in the range of 1 to 1000 microns. It is contemplated for the plurality of magnetic beads 22 to be received in a drop of a selected first fluid, as hereinafter described. The surfaces of the plurality of magnetic beads 22 are coated with a suitable ligand or receptor, such as antibodies, lectins or other bioreactive molecules, which can selectively bind analyte targets in the first fluid to the plurality of magnetic beads 22. Device 10 further includes upper plate 40 having upper and lower surfaces 42 and 44, respectively. Lower surface 44 of upper plate 40 includes first region 46 adapted for receiving the plurality of magnetic beads 22 thereon, as hereinafter described.

In operation, the plurality of magnetic beads 22 are deposited in the first fluid and the first fluid is mixed to facilitate the binding of the targets in the first fluid to corresponding magnetic beads 22. In addition, a plurality of particles 50 is added to the first fluid and mixed therein such that the plurality of magnetic beads 22 and the plurality of particles 50 form a mixture. Each of the plurality of particles 50 may have a different dimension that the dimensions of the plurality of magnetic beads 22. For example, the plurality of particles 50 may be spherical and have a diameter greater than the diameters of the plurality of magnetic beads. It is contemplated for the plurality of particles 50 to diameters in the range of 1 to 1000 microns, and preferably, approximately 200 microns. In addition, the plurality of particles 50 may be magnetic or non-magnetic. By way of example, if magnetic, the plurality of particles 50 may take the form of iron particles, magnetic beads or the like. Alternatively, the plurality of particles 50 may be coated in a magnetic material.

Once the plurality of magnetic beads 22 and the plurality of particles 50 are mixed within the first fluid, drop 56 of the first fluid is deposited on first region 20 of upper surface 16 of lower plate 14, in any conventional matter such as by a micropipette or like. In order to facilitate the transfer of the plurality of magnetic beads 22 having the targets bound thereto from drop 56 to the second location, namely, first region 46 of lower surface 44 of upper plate 40, upper plate 40 is positioned such that first region 46 of lower surface 44 of upper plate 40 is axially aligned with the first location, namely, first region 20 of upper surface 16 of lower plate 14, and hence, with drop 56. Lower surface 44 of upper plate 40 may be spaced from drop 56 by air gap 58 or in engagement with drop 56 without deviating from the scope of the present intention. A force generator, e.g, a magnetic force generator or a magnet 60, is positioned adjacent upper surface 42 of upper plate 40. It is contemplated for magnet 60 to be axially movable between a first position wherein magnet 60 is adjacent to upper surface 42 of upper plate 40 and a second position wherein magnet 60 is axially spaced from upper surface 42 of upper plate 40. With magnet 60 in the first position, as heretofore described, magnet 60 magnetically attracts the plurality of magnetic beads 22 having the targets bound thereto, as well as, the plurality of particles 50, if magnetic, in drop 56 and draws the plurality of magnetic beads 22 having the targets bound thereto, as well as, the plurality of particles 50, if magnetic, toward first region 46 of lower surface 44 of upper plate 40. More specifically, the magnetic force generated by the force generator or magnet 60 draws the plurality of magnetic beads 22 having the targets bound thereto, as well as, the plurality of particles 50, if magnetic, from drop 56 to the second location, i.e., first region 46 of lower surface 44 of upper plate 40. Any undesired (or unbound) material 54 in drop 56 is retained therein by the surface tension of drop 56.

It can be appreciated that if the plurality of particles 50 are magnetic and have dimensions greater than the dimensions of the plurality of magnetic beads 22, the larger plurality of particles 50 cause the entire aggregate (or in other words, the mixture of the plurality of magnetic beads 22 having the targets bound thereto and the plurality of particles 50) to be more magnetic. Thus, the entire aggregate is more easily drawn by the magnetic force of magnet 60 from first region 20 of upper surface 16 of lower plate 14 from drop 56 to first region 46 of lower surface 44 of upper plate 40. As heretofore described, the plurality of magnetic beads 22 having the targets bound thereto may be sticky and have a tendency to clump together at first region 20 of upper surface 16 of lower plate 14, thereby capturing contaminants and/or undesired material 54 within the clump. It is understood that the larger, plurality of particles 50 in drop 56 will be more responsive to the magnetic force generated by magnet 60 than the smaller, plurality of magnetic beads 22. As such, the plurality of particles 50 will travel from drop 56 at a higher velocity in response to the magnetic force generated by magnet 60 toward first region 46 of lower surface 44 of upper plate 40 than the plurality of magnetic beads 22 having the targets bound thereto. Therefore, as the plurality of particles 50 travel toward first region 46 of lower surface 44 of upper plate 40, the plurality of particles 50 cause any clump of the plurality of magnetic beads 22 having the targets bound thereto to break apart, thereby allowing for the contaminants and/or undesired material 54 captured within the clump of the plurality of magnetic beads 22 to be freed within drop 56. As a result, as the plurality of magnetic beads 22 having the targets bound thereto, as well as, the plurality of particles 50, if magnetic, are drawn from the first location (i.e., drop 56 on first region 20 of upper surface 16 of lower plate 14) to the second location (i.e., first region 46 of lower surface 44 of upper plate 40), the freed undesired (or unbound) material 54 in drop 56 is retained therein by the surface tension of drop 56.

In the event that a clump of the plurality of magnetic beads 22 having the targets bound thereto fails to break apart during the transfer from the first location (i.e., drop 56 on first region 20 of upper surface 16 of lower plate 14) to the second location (i.e., first region 46 of lower surface 44 of upper plate 40) such that contaminants and/or undesired material 54 remains captured within a clump of the plurality of magnetic beads 22 transferred to the second location, it is contemplated to repeat the process heretofore described. More specifically, it is contemplated to transfer the plurality of magnetic beads 22 having the targets bound thereto and the plurality of particles 50, if magnetic, from the second location, namely, first region 46 of lower surface 44 of upper plate 40, back to the first location, and subsequently back to the second location. For example, with upper plate 40 positioned such that first region 46 of lower surface 44 of upper plate 40 is axially aligned with first region 20 of upper surface 16 of lower plate 14, and hence, with drop 56, the force generator, e.g, magnet 60, may be positioned adjacent lower surface 18 of lower plate 14. With magnet 60 positioned adjacent lower surface 18 of lower plate 14, magnet 60 magnetically attracts the plurality of magnetic beads 22 having the targets bound thereto, as well as, the plurality of particles 50, if magnetic, at the second location, namely, first region 46 of lower surface 44 of upper plate 40, and draws the plurality of magnetic beads 22 having the targets bound thereto, as well as, the plurality of particles 50, if magnetic, toward the first location, namely, drop 56 on first region 20 of upper surface 16 of lower plate 14. As the aggregate (or in other words, the mixture of the plurality of magnetic beads 22 having the targets bound thereto and the plurality of particles 50) travels toward the first location, the plurality of particles 50 in the aggregate causes any clump of the plurality of magnetic beads 22 having the targets bound thereto to break apart, as heretofore described, so as to allow for the contaminants and/or undesired material 54 captured within the clump of the plurality of magnetic beads 22 to be freed.

Once the aggregate returns to the first location, it is contemplated to transfer the aggregate back to the second location, as heretofore described. Once again, it is noted that by transferring the plurality of magnetic beads 22 having the targets bound thereto, as well as, the plurality of particles 50, if magnetic, from the first location (i.e., drop 56 on first region 20 of upper surface 16 of lower plate 14) to the second location (i.e., first region 46 of lower surface 44 of upper plate 40), the plurality of particles 50 cause any clump of the plurality of magnetic beads 22 having the targets bound thereto to break apart, thereby allowing for the contaminants and/or undesired material 54 captured within the clump of the plurality of magnetic beads 22 to be freed within drop 56. As a result, it can be appreciated that the method heretofore described allows for the simple and inexpensive disaggregation of particles in a fluidic medium to facilitate the downstream analysis of an analyte target. The methodology of the present invention facilitates the disaggregation of particles in a fluidic medium without the use of an external agitation device, such as a pipette.

Alternatively, it is contemplated for the plurality of particles 50 to be inert, and hence, non-magnetic. As such, in order to facilitate the transfer of the plurality of magnetic beads 22 having the targets bound thereto from the first location, namely, the drop 56 on first region 20 of upper surface 16 of lower plate 14, to the second location, namely, first region 46 of lower surface 44 of upper plate 40, upper plate 40 is positioned such that first region 46 of lower surface 44 of upper plate 40 is axially aligned with first region 20 of upper surface 16 of lower plate 14, and hence, with drop 56. Lower surface 44 of upper plate 40 may be spaced from drop 56 by air gap 58 or in engagement with drop 56 without deviating from the scope of the present intention. A force generator, e.g., magnet 60, is positioned adjacent upper surface 42 of upper plate 40. It is contemplated for magnet 60 to be movable between a first position wherein magnet 60 is adjacent to upper surface 42 of upper plate 40 and a second position wherein magnet 60 is axially spaced from upper surface 42 of upper plate 40.

With magnet 60 in the first position, as heretofore described, magnet 60 magnetically attracts the plurality of magnetic beads 22 having the targets bound thereto in drop 56 and draws the plurality of magnetic beads 22 having the targets bound thereto toward first region 46 of lower surface 44 of upper plate 40. The plurality of particles 50, if non-magnetic, are not attracted to magnet 60. Hence, it can be appreciated that the non-magnetic, plurality of particles 50 captured within a clump of the plurality of magnetic beads 22 having the targets bound thereto remain relatively stationary within drop 56 as the plurality of magnetic beads 22 having the targets bound thereto are drawn towards first region 46 of lower surface 44 of upper plate 40. As the plurality of magnetic beads 22 having the targets bound thereto are drawn towards first region 46 of lower surface 44 of upper plate 40, the relatively stationary plurality of particles 50 captured within a clump of the plurality of magnetic beads 22 having the targets bound thereto act to break apart the clump as magnetic beads 22 are drawn towards magnet 60, thereby allowing for the contaminants and/or undesired material 54 captured within the clump of the plurality of magnetic beads 22 to be freed. More specifically, the magnetic force generated by the force generator or magnet 60 draws the plurality of magnetic beads 22 having the targets bound thereto from the first location, i.e., drop 56 first region 20 of upper surface 16 of lower plate 14 to the second location, i.e., first region 46 of lower surface 44 of upper plate 40. As such, any of the freed undesired (or unbound) material 54 in drop 56 is retained therein by the surface tension of drop 56.

Referring to FIGS. 3-4, an alternate device for effectuating the methodology of the present invention is generally designated by the reference numeral 70. Device 70 includes plate 74 having first and second surfaces 76 and 78, respectively. First surface 76 of plate 74 includes first region 80 adapted for receiving a plurality of magnetic beads 22 thereon, as hereinafter described. As heretofore described, each of the plurality of magnetic beads has a diameter in the range of 1 to 1000 microns. It is contemplated for first surface 76 of plate 74 and the plurality of magnetic beads 22 to be received in a selected fluid, as hereinafter described. For example, plate 74 may take the form of test tube wherein the inner surface of the test tube defines first surface 76. However, other configurations are possible without deviating from the scope of the invention.

In operation, the plurality of magnetic beads 22 are deposited in the fluid and the fluid is mixed to facilitate the binding of the targets in the fluid to corresponding magnetic beads 22. In addition, a plurality of particles 50 is added to the first fluid and mixed therein such that the plurality of magnetic beads 22 and the plurality of particles 50 form a mixture. As noted above, each of the plurality of particles 50 may have a different dimension that the dimensions of the plurality of magnetic beads 22. For example, the plurality of particles 50 may be spherical and have a diameter greater than the diameters of the plurality of magnetic beads. As previously described, it is contemplated for the plurality of particles 50 to diameters in the range of 1 to 1000 microns, and preferably, approximately 200 microns. In addition, the plurality of particles 50 may be magnetic or non-magnetic. By way of example, if magnetic, the plurality of particles 50 may take the form of iron particles, magnetic beads or the like. Alternatively, the plurality of particles 50 may be coated in a magnetic material.

Once the plurality of magnetic beads 22 and the plurality of particles 50 are mixed within the fluid, the fluid with the mixture of the plurality of magnetic beads 22, with the targets bound thereto, is brought into contact with first surface 76 of plate 74. A force generator, e.g., a magnetic force generator or a magnet 60, is positioned adjacent second surface 78 of plate 74. It is contemplated for magnet 60 to be axially movable between a first position wherein magnet 60 is aligned with first region 80 of first surface 76 of plate 74 and a second position wherein magnet 60 is aligned with a second region 82 of first surface 76 of plate 74, which is longitudinally spaced from first region 80. With magnet 60 in the first position, magnet 60 magnetically attracts the plurality of magnetic beads 22 having the targets bound thereto, as well as, the plurality of particles 50, if magnetic, to first region 80 of first surface 76 of plate 74, FIG. 3, to form aggregate 84. The plurality of magnetic beads 22 having the targets bound thereto capture the plurality of particles 50 and undesired (or unbound) material 54 within aggregate 84. To free any undesired (or unbound) material 54 within aggregate 84, magnet 60 is slid along second surface 78 of plate 74 from the first position in alignment with first region 80 of first surface 76 of plate 74 to the second position in alignment with second region 82 of first surface 76 of plate 74. As magnet 60 is slid from the first position to the second position, the magnetic force generated by the force generator or magnet 60 draws the plurality of magnetic beads 22 having the targets bound thereto, as well as, the plurality of particles 50, if magnetic, along first surface 76 of plate 74 thereby breaking apart aggregate 84 and freeing any undesired (or unbound) material 54 captured therein.

It can be appreciated that if the plurality of particles 50 are magnetic and have dimensions greater than the dimensions of the plurality of magnetic beads 22, the larger plurality of particles 50 cause the entire aggregate (or in other words, the mixture of the plurality of magnetic beads 22 having the targets bound thereto and the plurality of particles 50) to be more magnetic. Thus, the entire aggregate is more easily drawn by the magnetic force of magnet 60 along first surface 76 of plate 74. As heretofore described, the plurality of magnetic beads 22 having the targets bound thereto may be sticky and have a tendency to clump together at first region 80 of first surface 76 of plate 74, thereby capturing contaminants and/or undesired material 54 within aggregate 84. It is understood that the larger, plurality of particles 50 in aggregate 84 will be more responsive to the magnetic force generated by magnet 60 than the smaller, plurality of magnetic beads 22. As such, the plurality of particles 50 will travel along first surface 76 of plate 74 at a higher velocity in response to the magnetic force generated by magnet 60. Therefore, as the plurality of particles 50 travel toward second region 82 of first surface 76 of plate 74, the plurality of particles 50 and the plurality of magnetic beads 22 having the targets bound thereto break apart, thereby allowing for the contaminants and/or undesired material 54 captured within aggregate 84 to be freed and washed away.

In the event that movement of the plurality of magnetic beads 22 having the targets bound thereto\fails to sufficiently break apart during the transfer from the first location (i.e., first region 80 of first surface 76 of plate 74) to the second location (i.e., second region 82 of first surface 76 of plate 74) such that contaminants and/or undesired material 54 remain captured within a clump of the plurality of magnetic beads 22 transferred to the second location, it is contemplated to slid magnet 60 along second surface 78 of plate 74 back to its initial, first position in alignment with first region 80 of first surface 76 of plate 74. As magnet 60 is slid along second surface 78 of plate 74 from the second position in alignment with second region 82 of first surface 76 of plate 74 to the first position in alignment with first region 80 of first surface 76 of plate 74, the magnetic force generated by the force generator or magnet 60 draws the plurality of magnetic beads 22 having the targets bound thereto, as well as, the plurality of particles 50, if magnetic, along first surface 76 of plate 74 thereby breaking apart any remaining clumps and freeing any undesired (or unbound) material 54 captured therein. Thereafter, if the process for freeing any undesired (or unbound) material 54 is unsuccessful, the process may repeated, once again, to free any captured undesired (or unbound) material 54. In other words, once the aggregate returns to the first location, it is contemplated to transfer the aggregate back to the second location, as heretofore described. It can be appreciated that the back and forth movement of the plurality of magnetic beads 22 and the plurality of particle 50, if magnetic, along first surface 76 of plate 74 will break apart any clumps and free any captured undesired (or unbound) material 54 in aggregate 84.

If the plurality of particles 50 are inert, and hence, non-magnetic, it can be appreciated that the non-magnetic, plurality of particles 50 captured within aggregate 84 remain relatively stationary as the plurality of magnetic beads 22 having the targets bound thereto are drawn across surface 76 of plate 74 from the first location (i.e., first region 80 of first surface 76 of plate 74) to the second location (i.e., second region 82 of first surface 76 of plate 74). As the plurality of magnetic beads 22 having the targets bound thereto are drawn towards second region 82 of first surface 76 of plate 74, the relatively stationary plurality of particles 50 captured within aggregate 84 interfere with the movement of the plurality of magnetic beads 22 having the targets bound thereto and act to break apart aggregate 84 as the plurality of magnetic beads 22 are drawn towards the second location, thereby allowing for the contaminants and/or undesired material 54 captured within aggregate 84 of the plurality of magnetic beads 22 to be freed.

It can be appreciated that the above descriptions of the device and method are merely exemplary of the present invention. Various modes of carrying out the invention are contemplated as being within the scope of the following claims particularly pointing out and distinctly claiming the subject matter, which is regarded as the invention.

We claim:

1. A device for facilitating the disaggregation of targets in a biological sample, comprising:
    a mixture at least partially defined by:
        a plurality of solid phase substrates coated with receptors, the plurality of solid phase substrates having dimensions, being magnetic and being moveable in response to a magnetic force, the targets in the biological sample selectively bindable to the receptors of the plurality of solid phase substrates and at least a portion of the plurality of solid phase substrates defining an aggregation in the mixture; and
        a plurality of magnetic particles having dimensions greater that the dimensions of the plurality of solid phase substrate, the plurality of magnetic particles being free of receptors to which the targets selectively bind;
    a first plate having a first side defining a first supporting surface for supporting the mixture and a second side;
    a second plate positioned alongside the first plate and spaced from the first plate such that the first side of the first plate and the first side of the second plate are out of contact and define a gap therebetween, the second plate having a first side defining a second supporting surface directed at the first supporting surface and a second side; and
    a magnetic force generator generating a magnetic force, the magnetic force generator positionable adjacent the second side of the second plate such that the magnetic force acts on the plurality of magnetic particles and causes the plurality of magnetic particles in the mixture to travel through the gap between the first and second plates toward the second supporting surface, whereby the aggregation of the at least a portion of plurality of solid phase substrates in the mixture is disaggregated;
    wherein:
        the mixture is receivable on the first supporting surface prior to the magnetic force acting on the plurality of magnetic particles;
        the first and second plates are spaced such that at least a portion of the plurality of magnetic particles in the mixture are out of contact with both the first and second plates as the at least the portion of the plurality of magnetic particles in the mixture travels through the gap; and
        the aggregation of the at least a portion of plurality of solid phase substrates in the mixture is disaggregated by the plurality of magnetic particles travelling through the gap between the first and second plates.

2. The device of claim 1 wherein each of the plurality of particles has a dimension and each of the plurality of solid phase substrates has a dimension, the dimensions of the plurality of particles being greater than the dimensions of the plurality of solid phase substrates.

3. The device of claim 1 wherein each of the plurality of magnetic particles has an outer surface and a coating about the outer surface, the coating being magnetic.

4. The device of claim 1 wherein the plurality of solid phase substrates are magnetic beads.

5. The device of claim 1 wherein the plurality of magnetic particles are generally spherical.

* * * * *